(12) United States Patent
Deutsch

(10) Patent No.: US 8,320,634 B2
(45) Date of Patent: Nov. 27, 2012

(54) SYSTEM AND METHOD FOR MONITORING PROTECTIVE GARMENTS

(76) Inventor: Richard Deutsch, Annapolis, MD (US)

( * ) Notice: Subject to any disclaimer, the term of this patent is extended or adjusted under 35 U.S.C. 154(b) by 374 days.

(21) Appl. No.: 12/803,769

(22) Filed: Jul. 6, 2010

(65) Prior Publication Data

US 2011/0007950 A1 Jan. 13, 2011

Related U.S. Application Data

(60) Provisional application No. 61/270,661, filed on Jul. 11, 2009.

(51) Int. Cl.
*G06K 9/00* (2006.01)

(52) U.S. Cl. ........................... 382/111; 382/103

(58) Field of Classification Search ............... None
See application file for complete search history.

(56) References Cited

U.S. PATENT DOCUMENTS

| | | | |
|---|---|---|---|
| 5,376,963 A | 12/1994 | Zortea | |
| 5,838,839 A | 11/1998 | Seki | |
| 6,097,429 A | 8/2000 | Seeley | |
| 6,236,317 B1 * | 5/2001 | Cohen et al. | 340/573.1 |
| 6,252,598 B1 | 6/2001 | Segen | |
| 6,343,141 B1 | 1/2002 | Okada | |
| 6,642,956 B1 * | 11/2003 | Safai | 348/222.1 |
| 6,697,502 B2 | 2/2004 | Luo | |
| 6,707,486 B1 | 3/2004 | Millet | |
| 6,775,408 B1 | 8/2004 | Masaki | |
| 7,519,200 B2 | 4/2009 | Gokturk | |
| 7,612,666 B2 | 11/2009 | Badawy | |
| 2002/0090146 A1 | 7/2002 | Heger | |
| 2005/0265619 A1 | 12/2005 | Ozaki | |
| 2007/0237387 A1 | 10/2007 | Avidan | |
| 2008/0125288 A1 * | 5/2008 | Case | 482/1 |
| 2008/0253656 A1 | 10/2008 | Schwartzberg | |
| 2008/0298687 A1 | 12/2008 | Lai | |
| 2009/0091458 A1 * | 4/2009 | Deutsch | 340/573.1 |
| 2012/0146784 A1 * | 6/2012 | Hines et al. | 340/539.11 |

* cited by examiner

Primary Examiner — Andrew W Johns
Assistant Examiner — Siamak Harandi
(74) Attorney, Agent, or Firm — Thomas A. Kammer

(57) ABSTRACT

The wearing of required medical garments by caregivers and other persons is detected through the use of a digital imaging system and methods that employ digital imaging. The medical garments include colors, symbols or other features that allow them to be identified by the system. A moving object within an isolation room or other area requiring the wearing of medical garments is detected. Various stages of processing confirm that the moving object is indeed a person and that the person is wearing the required medical garments. In order to enhance the digital imaging procedure, the person may be instructed to move to a selected position.

23 Claims, 3 Drawing Sheets

SYSTEM AND METHOD FOR MONITORING PROTECTIVE GARMENTS

BACKGROUND OF THE INVENTION

1. Field of the Invention

The field of the invention relates to systems and methods for promoting the safety of health care workers and/or other persons by identifying and ensuring that the workers are wearing appropriate garments such as medical gowns, gloves and/or headwear when attending to selected patients.

2. Brief Description of the Related Art

Various pathogens are present within the hospital environment. These "superbugs" present a hazard to the patients residing within. CDC estimates hospital acquired infections account for two million inpatient infections a year with over 100,000 associated deaths at costs exceeding thirty billion dollars. Routine contact with numerous patients by their caregivers provides a robust opportunity to transfer these hospital "bugs" between patients. There have been numerous outbreaks of contagious superbug pathogens affecting large communities of hospital patients. These pathogens include Methicillin Resistant Staphylococcus Aureus (MRSA) and Clostridium difficile (C diff). Patients found to be harboring such diseases are typically referred to isolation rooms requiring the donning of protective gowns and gloves by anyone desiring entry into the affected patient's room. Alternately, those patients with compromised immune system due to disease or medical intervention require a similarly isolated sterile environment requiring all attending caregivers to be appropriately gowned and gloved.

Various identification systems have been developed for detecting human forms in general or specific individuals. One such system, as disclosed in US Pub. No. 2008/0298687 (incorporated by reference herein), detects human form and determines whether the detected person is allowed to pass into a selected area. U.S. Pat. No. 7,519,200, also incorporated by reference herein, provides a system for recognizing persons based on facial recognition, clothing and/or text. U.S. Pat. No. 6,097,429 discloses a surveillance system that distinguishes between human and non-human forms so that detection of the latter does not signal an intrusion. Systems have also been developed for tracking people in health care facilities. U.S. Pat. Nos. 7,612,666 and 6,727,818 disclose two such systems.

SUMMARY OF THE INVENTION

A system and method are provided for promoting sanitation for health care workers, patients and/or visitors by firstly electronically detecting the presence and possible identity of a caregiver and secondly electronically identifying the presence of one or more specific garments by their shape, color and/or displayed symbol. The system and method help assure proper wearing of a sterile medical gown and/or gloves and/or mask and/or head cover by health care workers prior to their contact or near contact with a patient. Such a system and method further help prevent the transfer of pathogens to or from the health care worker when attending to a patient with a medical condition requiring such protective precautions.

A system for promoting hygienic safety according to the invention includes a digital camera, an image processor operatively associated with the digital camera, and a logic program capable of determining whether a person is within a viewing area of the camera and is wearing a required medical garment. An annunciator is also provided for generating a message if a person is within the viewing area and a required garment has not been determined to be present by the logic program.

A method according to the invention helps ensure compliance with isolation room attire requirements. Such a method includes electronically detecting whether a person has entered a selected viewing area, electronically determining whether the person within the viewing area is wearing a required medical garment, and generating a message if the required medical garment is not determined as being worn. The method preferably further includes instructing the person to position himself to facilitate garment detection.

A method for determining whether a person is wearing a required protective medical garment in a selected area by detection of a characteristic feature (e.g. color, shape or a symbol) identifying the garment is also provided. The method includes providing a protective medical garment including a characteristic feature for identifying the protective garment, creating a digital image of the person within the selected area, instructing the person to move to a selected position within the selected area, and analyzing the digital image to determine whether it contains the characteristic feature.

DETAILED DESCRIPTION OF THE PREFERRED EMBODIMENTS

Figure 1:
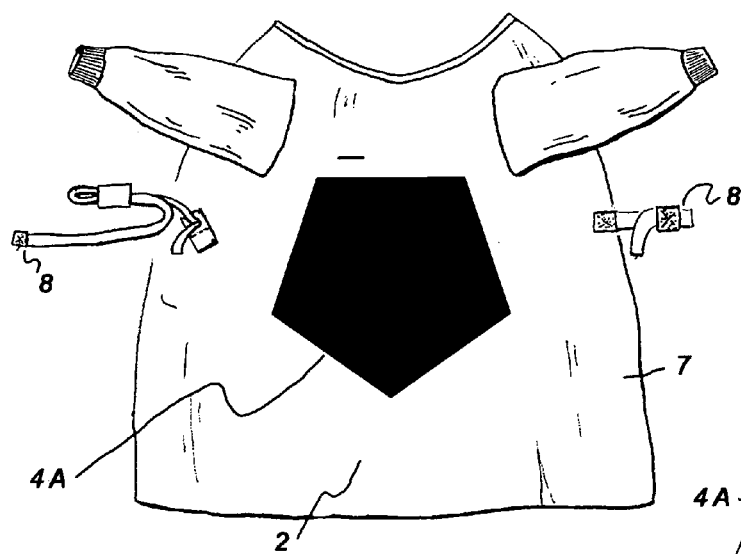
FIG. 1 illustrates a protective medical gown including symbol on its front surface.

A system and method are provided for ensuring that isolation room protocol regarding protective garments is safely followed. While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Figure 2:
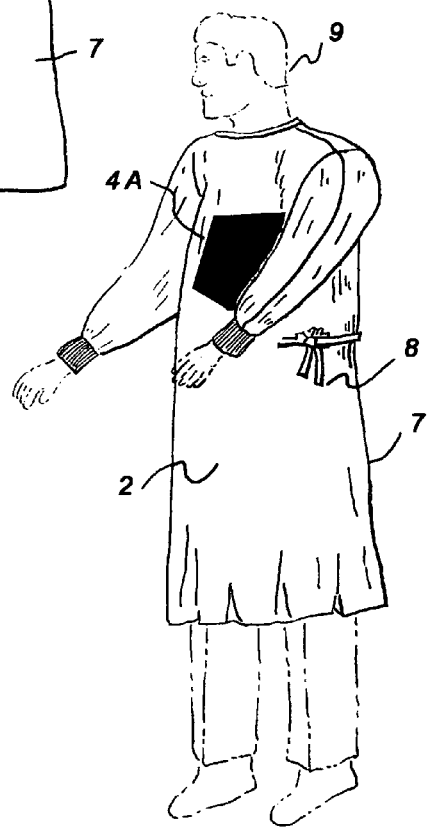
FIG. 2 illustrates a health care worker wearing a medical gown of the type shown in FIG. 1.

Referring to FIG. 1, a medical gown 7 of the type used in patient isolation rooms is shown. A caregiver 9 wearing such a gown is shown in FIG. 2. The gown includes a color 2 and a symbol 4A, either or preferably both of which may be used to identify that the garment is indeed a gown as well as possibly the identity of the person wearing the gown. As used herein, the term "color" may refer to an individual color, a color pattern, or a combination of colors. The identity of the person may be general in nature, distinguishing, for example, doctors and nurses, or specific to a particular nurse or doctor.

A system is provided that is preferably capable of initially determining the presence of a caregiver via a PIR (passive infrared) motion detector or more preferably by the change in a video image field (motion detection) as referenced by a digital imaging system. In order to minimize false triggering and artifact detection, the scale of such change in image field will be of such magnitude as to unlikely represent anything other than the human form, e.g. the system is non-reactive to motion of a patient assist ventilator. The system further is further preferably capable of determining a region on the captured image which corresponds to a torso, a hand and/or the head of the health care worker. Upon or subsequent to this anatomical area detection and analysis by the image processing system, it will then be determined if the particular area contains a specific color and/or other symbol such as a logo or indicia. The presence or absence of a color and/or symbol may be indicative of the general or specific identity of the caregiver, if identity information is desired, and the presence or lack thereof of the required medical gown and associated garments (e.g. mask and gloves) when the health care worker is attending to a patient. Image recognition as employed in optical glyph tracking can, for example, be used to identify a symbol associated with any gown or other medical garment. The detection of a symbol can also be employed to confirm the presence of a caregiver as opposed to some other moving object, providing redundancy to the detected change in the video image field described above or operating independently. Color detection can be used for the same purpose, but may not be as reliable as symbol detection for confirming the presence of a person. An annunciator provides an audible or visual indication of the presence or absence of the anticipated color, symbol or other characterisitic feature of the required medical garment.

Various systems have been developed for recognizing colors and symbols and would be usable for the purposes of the present invention. Color detection and reference comparison are described by Luo in U.S. Pat. No. 6,697,502, which is incorporated by reference herein. Symbol detection and reference comparison are described in U.S. Pub. No. 2008/0253656A1 to Schwartzberg and is incorporated by reference herein. Systems have also been developed for recognizing human form, clothing and text, as discussed above in the Background section of this application. Such systems are also usable in certain applications of the present invention.

Figure 6:
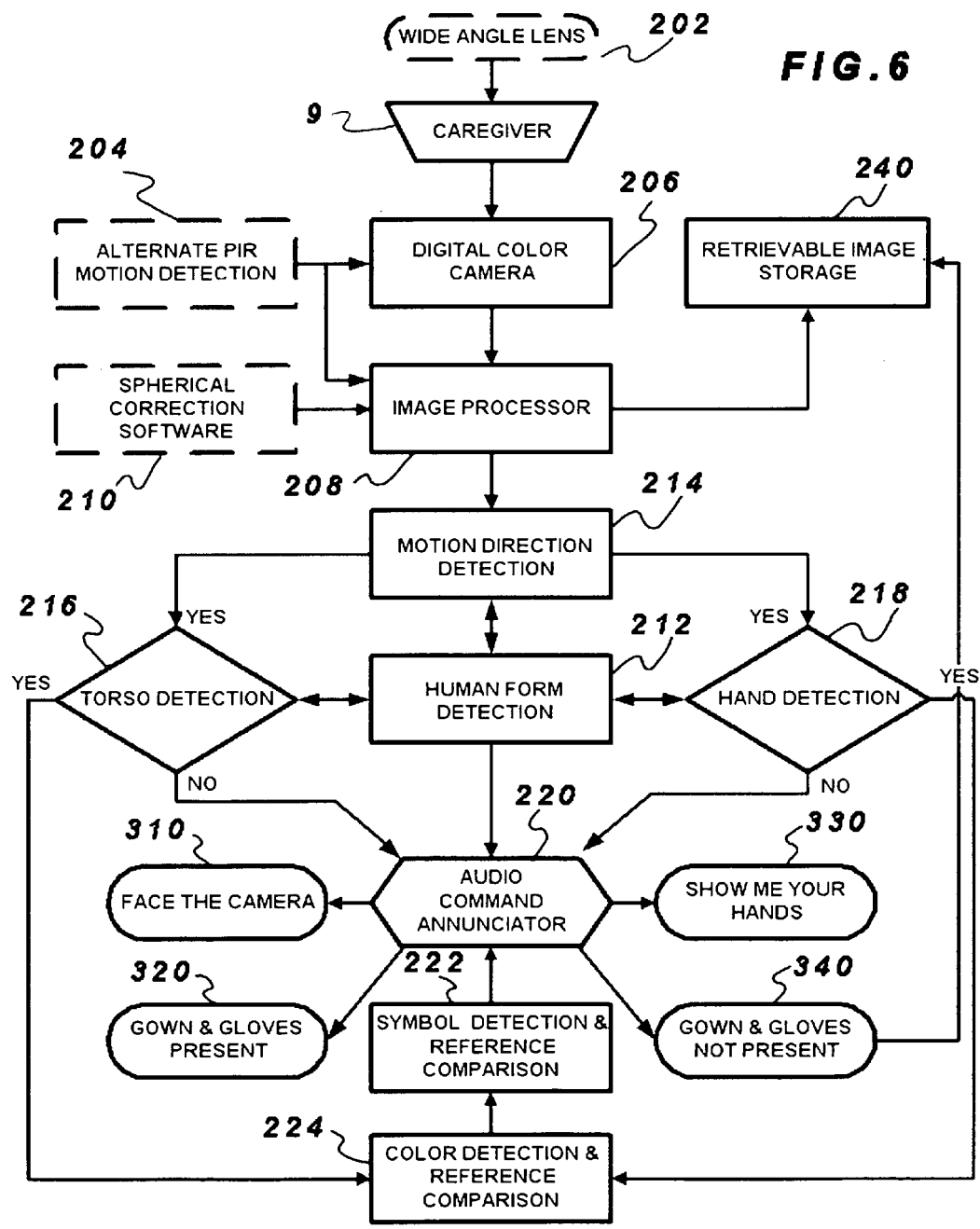
FIG. 6 is a flowchart of operation of the hardware, processors and software for detecting the presence of a health care worker, capturing his/her image, analyzing the composition of the image, detecting and comparing specific components of the image to a reference data base and indicating the presence or lack thereof of a medical gown and gloves.

The preferred embodiment of the system, shown in FIG. 6, includes a digital image recognition system that incorporates a digital color camera 206 arranged to view a scene through a wide angle fish eye lens 202. The viewed scene would include a caregiver 9 such as a health care worker (HCW) or visitor in an isolation room, but preferably does not include the patient. An image processor 208 associated with motion direction detection software 214 and a human form recognition processing routine 212 controls routine stages 216 and 218 that isolate an image of the torso and hands of the detected person. Stage 224 evaluates the image of the torso and/or hands to determine if the associated colors match a predetermined library of acceptable colors. Stage 222 determines if a specific symbol (e.g. logo or other indicia) associated with a specific color and body part is present. The symbol can itself identify the medical garment in the absence of color and body part analysis. Command annunciator 220 provides audible or visual cues relating to the final determination as to whether compliance with protective garment protocol has been met. While the annunciator preferably provides audible and/or visual feedback to the caregiver under observation, it may also function as a means of wirelessly communicating directly or indirectly to a receiver (not shown) at a remote location information relating to the presence of a caregiver and his/her compliance or noncompliance with protective garment protocol. The annunciator may be comprised of a system including one or more elements that may or may not be used to perform the same functions. For example, one element of the annunciator may be used to indicate the absence of a medical garment while another element may be used to instruct the caretaker. It is also possible to use all elements of the annunciator to provide all messages required by the garment monitoring system.

Image correction software 210 that will allow the image processor 208 to correct for spherical aberrations from the wide angle lens 202 may be associated with the image processor. U.S. Pub. No. 2005/0265619, incorporated by reference herein, discloses a device that may be used to reduce such aberrations. A retrievable image storage mechanism 240, such as a compact flash/SD card, is provided to capture and retain one or more images of the caregiver who fails to demonstrate the required protective garment(s) when detected and imaged by the monitoring system. Alternatively, the system may wirelessly transmit these images to a receiver (not shown) at a remote location.

The preferred embodiment of the invention provides an intelligent person, color and symbol recognition system and method for determining the presence of protective medical garments that are to be worn in special environments. The digital imaging system electro-optically detects and recognizes the presence or absence of a person within a patient's room. More specifically, it determines whether a person is within a predetermined viewing area of the digital camera within the patient's room. It operably associates that function with an electro-optical identification system able to recognize and classify specific protective garments by recognizing and identifying colors and/or symbols associated with such garments in order to determine and indicate their presence or absence as well as possibly identifying the person himself or the professional classification of the wearer.

The system provided by the invention provides robust protective garment identification for surveillance of a patient's hospital room that runs on a stand-alone or integral color camera, image processor, memory and associated software. To meet accuracy and speed requirements, hierarchical classifiers and coarse to fine search techniques are applied at each recognition stage for localization, segmentation and classification of the resulting image. Efficient hierarchical decomposition of a recognition task is employed involving coarse segmentation and classification methods. Ambiguous patterns may be forwarded to auto commands for instructing the caregiver to move and orient himself/herself via audio and/or visual commands so as to enhance image quality and detection. Given multiple segmentation hypotheses, the reliable recognition task is preferably accomplished by employing a convolutional network.

It should be understood that the elements shown in FIGS. 1-4 may be implemented in various forms of materials, shapes and configurations according to need or preference. The system depicted in FIG. 6 may be implemented in various forms of hardware, software or combinations thereof. The elements of FIG. 6 are preferably implemented in software on one or more appropriately programmed general purpose digital processing units having a processor and memory and input/output interfaces. While garment identification preferably involves conducting all of the steps shown in FIG. 6, a garment could be identified by just detecting a symbol that identifies that garment. The steps of human form detection, torso/hand detection and color detection would be omitted in this simplified procedure.

As discussed above, FIG. 1 provides an illustrative representation of a protective gown 7 to be worn by caregiver or visitor while in close approximation to a patient. Straps 8 are provided for securing the gown to the person. A prominently displayed character or symbol 4A is provided on the chest portion of the gown where it can easily be detected by the digital camera 206. The symbol 4A may be also or alternatively be displayed on the back (not shown) and/or one or more other visible surfaces of the medical gown 7. If used in multiple locations, it is more likely to be detected by the camera regardless of the orientation of the caregiver. In addition to being used to identify that the caregiver is wearing the required garment, the color and/or symbol may be used to identify whether the person is a doctor, nurse, aide or visitor. Different colors or symbols may be employed to differentiate individuals or classes of individuals through either electronic detection and analysis or simple observation.

FIG. 2 is an illustrative representation of a caregiver 9 wearing the medical gown 7. The color 2 allows for ease of detection by monitoring system. The symbol 4A in this illustrative embodiment is used for electronically identifying the specific protective item. Different symbols may be used to electronically distinguish between different types of garments, such as between gowns and gloves or between different types of gowns. Color can also be used to distinguish between garments, providing redundancy with the symbols to enhance accuracy of garment detection. Colors and symbols on a particular garment can be used to convey the same information, serving redundant functions, or to convey different information so long as at least one of them can be processed for the purpose of garment identification by the monitoring system.

Figure 3:
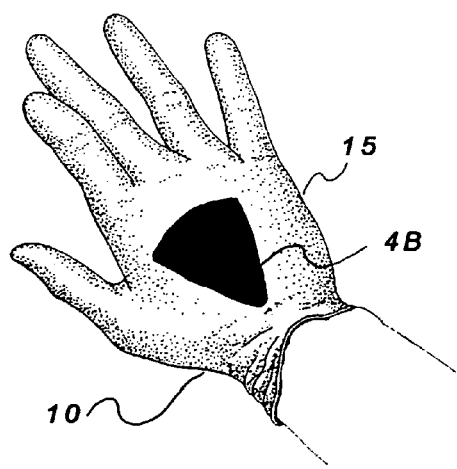
FIG. 3 illustrates a protective glove that includes a symbol on its dorsal surface.

FIG. 3 shows a protective glove 10 having a selected color 15 that is preferably different from the color 2 of the medical gown for ease of electronic recognition by the detection system. It further includes a second symbol 4B on its dorsal surface. The second symbol 4B is preferably different from the symbol 4A used to identify medical gowns. It will be appreciated that the palmer surface (not shown) of the glove may be provided with the second symbol in addition to or as an alternative to the location shown in the drawing.

Figure 4:
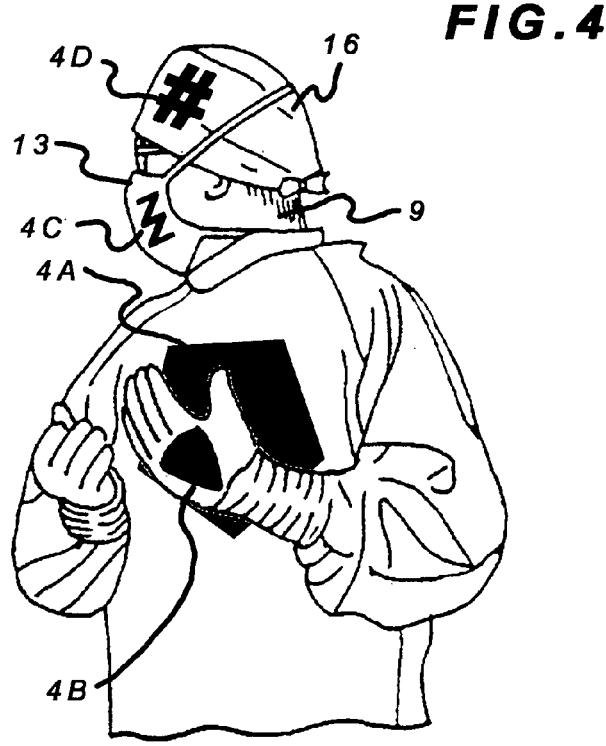
FIG. 4 illustrates a health care worker wearing a gown with a first detectable symbol, gloves with a second detectable symbol, a mask with a third detectable symbol, and a hat with a fourth detectable symbol.

FIG. 4 shows a caregiver wearing a protective mask 13 and head covering 16 as well as a gown and gloves. The mask bears a third symbol 4C while the head covering includes a different fourth symbol 4D. The mask and head covering are made from fabrics having colors that can be recognized by the system during its garment identification procedure.

Figure 5:
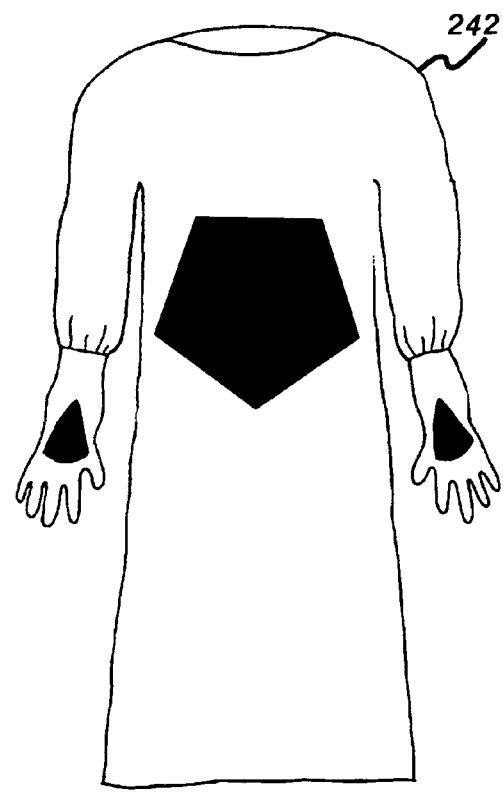
FIG. 5 illustrates a representation of an image with imaging details of the background removed that may be present in a database and used for determining whether matching garments are worn by a health care worker.

FIG. 5 illustrates a representation of a size corrected, difference image 242. The difference image is an image of the detected protective garments (gown and gloves) with images of the background and caregiver removed by image processing. This sub-image is presented for classification in the symbol detection and reference comparison stage 222 for final determination of the presence of detectable protective gown and gloves.

As discussed above, FIG. 6 schematically illustrates the preferred system and provides a flow diagram of the preferred method employed for determining whether a protective garment is worn when a person visits or attends to a patient. The wide angle optical lens 202 is affixed to the digital color camera 206. It is preferably positioned in a patient's room, which may be an isolation room, such that it views the caregiver 9 prior to and/or during treatment of the patient without detecting the patient himself. The caregiver should be viewed at least from the waist up within a predetermined viewing area of the digital camera. The predetermined viewing area may not include everything viewed by the lens 202, but rather a specific area of the patient's room. Corrective software 210 associated with the image processor 208 may be provided that can correct spherical distortions caused by wide angle, fisheye lenses such as the lens 202. The image processor 208 is operatively associated with a logic program including software routines and memory to perform multi-resolution image analysis. Different resolutions of the image are checked to assist in object recognition. Initial resolution is defined by detection of any large, presumably human object changing the background scene as determined by the motion direction detection routine 214. A system for detecting directional motion is disclosed in U.S. Pat. No. 6,707,486 to Millet et al., the disclosure of which is incorporated by reference herein. Human form detection by routine 212 further refines the detection scheme as coarse localization homes in on the human form within the captured image to reduce the number of pixels and thereby reduce the computational complexity. Edges of the image are computed and a saliency map (not shown) is generated. After successful localization and multiple segmentations, the saliency map blends edges to achieve intensity regions in the image. Highest peak values in the intensity regions have the highest probability of being the subject caregiver and are selected for further processing. Based on local edges and regional features, a refinement of an area of interest is determined for localization in the torso detection routine 216 and hand detection routine 218. Hand detection routines are disclosed, for example, in U.S. Pub. No. 2002/0090146 to Heger and U.S. Pat. No. 6,252,598 to Segen, both of which are incorporated by reference herein. Segmentation provides locations that are likely to include the desired items to be detected. This includes addressing illumination effects, positions, rotations, and distances of the caregiver from the camera. Comparisons to normalized correlation models or templates are performed to find similar illuminations, distances, orientations etc. in order to facilitate the removal of the ambient background from the image. To reduce illumination effects on the image, before classification, each sub-image is normalized with respect to brightness and contrast. This sub-image 242 minus the ambient background preferably has a fixed sized as illustrated in FIG. 5. Since the segmentation process itself is inherently ambiguous, it has to be tightly coupled to the garment item's shape for identification.

After successful localization, multiple segmentation hypotheses are created by an algorithm based on non linear projections onto a baseline image. The recognition system preferably employs a convolutional neural network classifier or other statistical classifier which identifies each associated medical garment and returns a confidence value for each item detected. Based on the confidence measure, the segmentation hypotheses with the highest overall confidence may be accepted or, if the confidence level does not meet a predetermined level of reliability, the audio command annunciator 220 may issue instructions 310 and/or 330 to the detected caregiver 9 instructing him to alter his position or orientation with respect to the camera 206 so as to improve the quality of the image undergoing analysis. Such instructions can also be provided upon the first detection of human motion within the room or selected area within the room so that the caregiver can immediately assume a position that is conducive to garment detection.

The fine localization of the sub-image based on segmentation and edge detection creates an image that is processed by the color detection and reference comparison routine 224.

Such comparison is accomplished by analyzing the color histograms of the sub-image to a reference table reflecting color composition of the anticipated specific protective item. The positive correlation of the color of the sub-image to a specific color pattern contained within the color reference table is of interest to the system as it indicates a high probability of the presence of the desired protective garment. When color correlation has been established, the sub-image undergoes additional analysis for the presence of a specific symbol by the symbol detection and reference comparison routine 222. As discussed above, digital imaging processing systems for detecting and analyzing colors and symbols are disclosed in U.S. Pat. No. 6,697,502 and U.S. Pub. No. 2008/0253656, respectively.

Upon successfully completing the aforementioned steps of matching subsets of image content comparisons, the command annunciator 220 will provide an announcement 320 and an activation control signal indicating successful compliance with the protective garment requirements. Alternately, if the monitoring system is unable to confirm the presence of the required garments after detection of the caregiver and completing image analysis, a control signal is transmitted to a co-operating receiver (not shown) as well as causing an announcement 340 by the audio command annunciator 220 indicating lack of compliance with protective garment rules. Additionally, the presence of the caregiver violating protocol without proper protective garments will be documented by a series of images to be recorded on a removable memory 240 associated with image processor 208 for future administrative action. Alternately, images of the violator may be transmitted wirelessly to a remotely located central computer system (not shown) for observation, storage and action.

A PIR based motion detector 204 may be included in addition to the system as described as a means to conserve energy and minimizing wear on the system. Requiring minimal power to function, this addition will awake the aforementioned camera 206 and image processor 208 from a power conserving sleep state when initially detecting motion by a caregiver in the area under surveillance.

A digital color camera is described by U.S. Pat. No. 6,642,956 Safai, which is incorporated by reference herein. Such a camera may be employed as the camera (206) in the system described herein.

The garment monitoring system discussed herein may be incorporated into a hygiene monitoring system as described in International Application No. PCT/US 09/00444, which is incorporated by reference herein. A touch sensor is disclosed in this application for detecting when a patient or bed is actually touched. It may alternatively be incorporated in other known hospital monitoring systems such as disclosed by Wildman in U.S. Pat. No. 6,727,818, by Lane in U.S. Pat. No. 6,975,231, by Cohen in U.S. Pat No. 6,236,317 or by Winings et al. in U.S. Pat. No. 6,882,278.

What is claimed is:

1. A system for promoting the hygienic safety of health care workers and patients, comprising:
   a digital camera;
   an image processor operatively associated with the digital camera;
   a logic program operatively associated with the image processor and capable of determining whether a person is within a predetermined viewing area of the digital camera and whether the person is wearing a required medical garment;
   an annunciator for generating a message if a person is determined to be within the predetermined viewing area of the digital camera and a required medical garment has not been determined to be present by the logic program.

2. A system as described in claim 1 wherein the logic program includes a stage for determining whether a required color is present in determining whether the person is wearing the required medical garment.

3. A system as described in claim 2 wherein the logic program includes a stage for determining whether a required symbol is present in determining whether the person is wearing the required medical garment.

4. A system as described in claim 1 wherein the logic program is capable of causing the annunciator to instruct a health care worker to move into a required position within the predetermined viewing area to facilitate medical garment detection.

5. A system as described in claim 1 wherein the logic program includes a stage for determining whether a required symbol is present in determining whether the person is wearing the required medical garment.

6. A system as described in claim 5 wherein the stage for determining whether the required symbol is present includes a symbol detection and reference comparison stage.

7. A system as described in claim 1 including a system for determining whether there is motion within a field of view of the digital camera that is most likely attributable to human motion.

8. A system as described in claim 7 wherein the logic program includes a stage for determining a human form and one or more specific parts of a human form.

9. A system as described in claim 8 wherein one of the specific parts includes the torso.

10. A system as described in claim 8 wherein the logic program includes a stage for color detection and reference comparison and a stage for symbol detection and reference comparison for determining, respectively, whether a person within the viewing area is wearing a required medical garment having a required color and bearing a required symbol.

11. A method for ensuring a health care worker or other person is properly attired with a required medical garment having a characteristic feature before attending to a patient, comprising:
    electronically detecting whether a person has entered a selected area that requires the wearing of the required medical garment;
    electronically determining whether the person within the selected area is wearing the required medical garment having the characteristic feature, and generating a message if the person is detected within the selected area and the required medical garment having the characteristic feature has not been determined as being worn by the person.

12. A method as described in claim 11 wherein the step of electronically detecting whether a person has entered a selected viewing area includes processing changes in an image field to detect motion likely due to movement of a human form.

13. A method as described in claim 12 wherein the step of electronically detecting whether a person has entered a selected viewing area includes a motion direction detection routine.

14. A method as described in claim 13 wherein the step of electronically detecting whether a person has entered a selected viewing area includes a human form detection routine.

15. A method as described in claim 14 including the step of electronically identifying one or more elements of the human form.

16. A method as described in claim 15 including the step of electronically determining whether a selected element of the human form includes a required symbol representative of a required medical garment.

17. A method as described in claim 15 including the step of electronically determining whether a selected element of the human form includes a required color representative of a required medical garment.

18. A method as described in claim 11 wherein the selected area includes a patient and wherein the person is detected without detecting the patient.

19. A method as described in claim 11 including the step of instructing an electronically detected person to move to a selected position to facilitate garment detection.

20. A method for determining whether a person is wearing a required medical garment in a selected area, comprising:
  providing a medical garment including a characteristic feature for identifying the protective garment;
  detecting a person within the selected area;
  creating a digital image of the person within the selected area;
  instructing the person to move to a selected position within the selected area likely to improve the quality of the digital image, and
  analyzing the digital image to determine whether it contains the characteristic feature identifying the garment.

21. A method as described in claim 20 wherein the selected area is an isolation room including a patient, including the step of detecting the person without detecting the patient.

22. A method as described in claim 20 wherein the medical garment is a medical gown including the step of electronically sending a message to the person if the characteristic feature identifying the gown is not determined to be present in the digital image.

23. A method as described in claim 20 wherein the characteristic feature is a symbol.

* * * * *